(12) United States Patent
Nilsen

(10) Patent No.: US 6,762,292 B2
(45) Date of Patent: Jul. 13, 2004

(54) OPTIMALLY LABELED OLIGONUCLEOTIDES

(75) Inventor: Thor W. Nilsen, Haddonfield, NJ (US)

(73) Assignee: Poly Probe, Inc., Philadelphia, PA (US)

( * ) Notice: Subject to any disclaimer, the term of this patent is extended or adjusted under 35 U.S.C. 154(b) by 0 days.

(21) Appl. No.: 09/911,039

(22) Filed: Jul. 23, 2001

(65) Prior Publication Data

US 2002/0012972 A1 Jan. 31, 2002

Related U.S. Application Data

(63) Continuation of application No. 09/482,803, filed on Jan. 13, 2000, now abandoned, which is a continuation of application No. 08/909,539, filed on Aug. 12, 1997, now Pat. No. 6,046,038, which is a continuation-in-part of application No. 08/657,961, filed on Jun. 4, 1996, now Pat. No. 6,072,043.

(51) Int. Cl.[7] .................. C07H 21/00; C07H 21/02; C07H 21/04; C12Q 1/68; C12P 19/34

(52) U.S. Cl. .................. 536/23.1; 536/22.1; 536/24.3; 536/24.33; 536/25.3; 536/25.32; 536/26.6; 435/6; 435/91.1; 435/91.2

(58) Field of Search .................. 435/6, 91.1, 91.2; 536/22.1, 23.1, 24.3, 24.33, 25.3, 25.32, 26.6

(56) References Cited

U.S. PATENT DOCUMENTS

| | | |
|---|---|---|
| 5,175,270 A | 12/1992 | Nilsen et al. |
| 5,403,708 A | 4/1995 | Brennan et al. |
| 5,487,973 A | 1/1996 | Nilsen et al. |
| 5,652,099 A | 7/1997 | Conrad |
| 6,046,038 A | 4/2000 | Nilsen |
| 6,072,043 A  * | 6/2000 | Nilsen ........................ 536/22.1 |

OTHER PUBLICATIONS

New England Biolabs Catalog, (New England Biolab Inc., Beverly, MA), p. 97, 1993.

* cited by examiner

Primary Examiner—Jezia Riley
(74) Attorney, Agent, or Firm—Lerner, David, Littenberg, Krumholz & Mentlik, LLP

(57) ABSTRACT

A method for the preparation of optimally labeled oligonucleotides wherein label-conjugated nucleotide triphosphates are incorporated into a nucleic acid sequence in a defined repetitive manner which allows for the optimal specific detectability of the oligonucleotide. The oligonucleotides of the present invention are useful in the assay of a wide variety of nucleic acid sequences, specifically wherever labeled nucleic acid probes are desired.

21 Claims, 5 Drawing Sheets

OPTIMALLY LABELED OLIGONUCLEOTIDES

CROSS-REFERENCE TO RELATED APPLICATIONS

This application is a continuation of U.S. application Ser. No. 09/482,803, filed Jan. 13, 2000, now abandoned, which is a continuation of U.S. application Ser. No. 08/909,539, filed Aug. 12, 1997, now U.S. Pat. No. 6,046,038, continuation-in-part of U.S. application Ser. No. 08/657,961, filed Jun. 4, 1996, now U.S. Pat. No. 6,072,043, which is incorporated herein by reference.

FIELD OF THE INVENTION

This invention relates to the preparation and use of labeled oligonucleotides. More particularly, it relates to methods of preparing and using oligonucleotides wherein label-conjugated nucleotides are incorporated into a nucleic acid sequence in a defined repetitive manner which allows for optimum detectability.

BACKGROUND OF THE INVENTION

Several publications are referenced in this application, with full citations appearing in the text of the specification. These references describe the state-of-the-art to which this invention pertains, and are hereby incorporated herein by reference.

Many different compounds have been used to detect nucleic acids. Broadly, labels of nucleic acids can be divided into two classes: (1) those which covalently modify nucleic acids with a detectable moiety, and (2) those which non-covalently modify nucleic acids with a detectable moiety, i.e., by ionic interactions, hydrogen-bonding, or intercalation. In general, non-covalent probes of nucleic acids exhibit dramatically increased detectability upon binding to nucleic acids, and consequently, have been very useful in assays designed to determine the total nucleic acid present in a given sample. In addition, non-covalently bound molecules can, and will, migrate from a labeled strand to an unlabeled one. Covalently bound molecules, on the other hand, can not migrate from a labeled oligonucleotide to an unlabeled one. Therefore covalently bound moieties are preferred for use as tagged nucleic acid probes.

Examples of compounds which have been covalently attached to nucleic acid sequences include conjugates between nucleotide triphosphates or phosphoramidites and labeling moieties, and directly reactive dyes, e.g. fluorescent moieties. Nucleotide triphosphates are incorporated into a nucleic acids by nucleic acid polymerases. Commercially available nucleotide triphosphates-dye conjugates include dCTP-Cy3, dCTP-Cy5, dUTP-FluorX, etc. available from DuPont, Molecular Probes, Boehringer Mannheim, and Amersham Life Sciences. Such dye conjugates contain cyanine or fluorescein derivatives which are covalently bound to the nucleotide, and each dye conjugate differs with respect to the absorbance maxima of the dye moiety. Directly reactive dyes covalently bind to an existing nucleic acid sequence. A few reactive dyes are commercially available, including various psoralens and ethidium mono- and di-azides.

The chemistry associated with conjugates of phosphoramidites and labeling moieties has dramatically improved in recent years allowing for the complete synthesis of labeled oligonucleotides with commercially available nucleic acid synthesizers. Labeled oligonucleotides have also been synthesized by a combination of modified phosphoramidites and reactive dyes, typically involving the incorporation of primary amines in the oligonucleotide during synthesis followed by covalent coupling of the amine groups to a reactive dye.

Of the three methods for the covalent linkage of labeling moieties to oligonucleotides, the nucleotide triphosphate-dye conjugates offer the greatest flexibility and the highest achievable specific detectability, i.e. fluorescence. Synthetic nucleic acids (molecules produced non-enzymatically) are generally limited to less than 100 bases and are subject to variable dye coupling chemistries. Directly reactive dyes, such as ethidium monoazide, react non-specifically and can potentially damage the labeled oligonucleotide. Polymerase-driven labeling, on the other hand, can produce molecules from a few tens of bases to several kilobases, can utilize standard labeling methods such as nick translation and primer extension reactions, and the degree of dye incorporation can be roughly controlled by varying the ratio of labeled NTP to unlabeled NTP.

The primary limitation of polymerase-driven labeling of nucleic acids is the absence of absolute control of the amount of label incorporated into a particular sequence. For example, if one desires to label DNA with dCTP-Cy3 and the specific sequence has only a limited number of "C" sites, then the resulting labeled oligonucleotide will have relatively few Cy3 molecules and consequently a low specific fluorescence. The present invention overcomes this sequence specific limitation and optimizes the incorporation of the label by polymerase.

SUMMARY OF THE INVENTION

The invention provides a method for the preparation and purification of optimally labeled oligonucleotides comprising the steps of (a) preparing a primer; (b) preparing a template oligonucleotide containing a nucleotide sequence complementary to the primer, and a nucleotide repeat region downstream from the complementary region; (c) annealing the template and primer in a suitable reaction medium containing a polymerase, nucleotide triphosphates and label-conjugated nucleotide triphosphates; (d) initiating synthesis of a complementary strand on the template; (e) attaching the oligonucleotide containing a target sequence adjacent to the complementary strand; and (f) purifying the optimally labeled oligonucleotide by any appropriate method.

The invention provides a method for preparing optimally labeled oligonucleotides comprising (a) preparing a template having a primer binding region, a 5' extension region for the incorporation of label-conjugated nucleotide triphosphates, and a 3' overhang region; and (b) labeling an oligonucleotide target sequence by denaturing the target sequence, adding excess template, dNTPs and polymerase in a suitable reaction medium.

The invention also provides an oligonucleotide comprising a nucleotide sequence complementary to a primer, and a nucleotide repeat region downstream from said complementary sequence, wherein the nucleotide repeat region comprises $N^r$ where $N^r$ is any nucleotide which can form a base pair with a label-conjugated nucleotide triphosphate, and optionally, a plurality of nucleotides, N, which are not capable of forming a base pair with a label-conjugated nucleotide triphosphate.

The invention further provides an optimally labeled oligonucleotide comprising a radiolabeled nucleic acid sequence and a nucleotide repeat region, wherein the nucleotide repeat region comprises $N^r$ where $N^r$ is any nucleotide which is conjugated to a label, and optimally, a plurality of nucleotides, N, which are not conjugated to a label.

These and other embodiments are disclosed or are obvious from the following detailed description.

DETAILED DESCRIPTION OF THE INVENTION

Figure 1A:
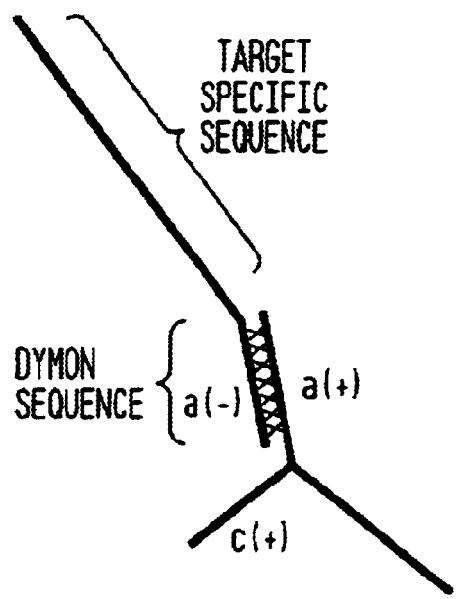
FIGS. 1A and B are a schematic representation of the addition of specificity and label to core dendrimers.

In order to more clearly understand the invention, certain terms are defined as follows.

The "complement" to a first nucleotide sequence is well known to be a second sequence comprising those bases which will pair by Watson-Crick hybridization with the first sequence. Thus, the complement to the deoxyribonucleic acid (DNA) sequence 5'-ATGC 3' is well known to be 5'-GCAT 3'. For duplex, or double stranded DNA, each of the two strands are described as complementary to the other or as a complementary pair. The terms complement and anticomplement may also be used. With reference to the identification of the strand of duplex DNA from which transcription to RNA proceeds, the transcription strand is generally described as plus and its complement as minus (or "+" and "−"), or the transcription strand may be described as the sense strand, and its complement as antisense. Two strands each hybridized to the other having all base pairs complementary, are 100% complementary to each other. Two strands, each hybridized to the other, having 5% of bases non-complementary, are 95% complementary (or the two strands have 95% complementarity).

A "probe" is a single or double stranded nucleic acid which has a sequence complementary to a target nucleic acid sequence of interest and which has some additional feature enabling the measurement of the probe-target duplex. The artisan will understand that if the probe and/or the target is double stranded, the double stranded nucleic acid must undergo strand separation before hybridization can take place.

A probe is rendered detectable by an attached tag or label. A tag or label linked to a probe may include, in principle, a fluorescent or luminescent tag, an isotopic label, a dye label, an enzyme label, an antigen determinant detectable by an antibody, or a binding moiety such as biotin enabling yet another moiety such as a streptavidin coated bead to specifically attach the probe. When the labeled or tagged probe-target duplex is formed, that duplex may be detected by the characteristic properties of the tag or label. The probe with its label moiety anneals to the target by hybridization and duplex formation allowing detection by a label.

A "primer" is a relatively short segment of oligonucleotide which is complementary to a portion of the sequence of interest (the sequence of interest can be a subfragment within a larger nucleic acid sequence). A primer represents the 5' terminus of the resulting extension product. A primer which is complementary to the sequence of interest on the template strand enables the 3' terminus to be acted on by a polymerase. A primer may also be modified at its 5' end with a binding moiety or detectable label.

"Hybridization" describes the formation of double stranded or duplex nucleic acid from complementary single stranded nucleic acids. Hybridization may take place between sufficiently complementary single stranded DNA and/or RNA to form: DNA-DNA, DNA-RNA or RNA-RNA.

The in vitro amplification of DNA is catalyzed by DNA polymerase. A number of types of DNA polymerase are known in the art. They generally share the common property of catalyzing the synthesis of a double stranded DNA sequence utilizing a single stranded template to which a primer is annealed. DNA polymerases extracted from most organisms become inactive at the temperatures required for thermal denaturing of nucleic acids. Thus, replacement of the enzyme at the start of each thermal cycle, or the addition of a factor able to prevent heat inactivation, is required if such heat sensitive enzymes are utilized. The DNA polymerases which are preferred for in vitro PCR as well as for the invention are derived from organisms which thrive at high temperatures and thus are heat resistant, i.e., thus maintain adequate catalytic activity at the temperature which denatures duplex DNA.

The reaction catalyzed by DNA polymerase is known to the art, and referred to herein as the "DNA polymerase reaction." The reaction requires some or all of the four deoxyribonucleotide triphosphates and primers, preferably in molar excess, and a means for cyclic strand separation. Strand separation is preferably achieved by thermal cycling between annealing and denaturation temperatures. Reverse transcriptase is known to mediate both RNA and DNA copying, as well as DNA to DNA copying. Hence, any number of enzymes now known will catalyze the polymerization reaction.

"Optimal spacing" describes that distance between labeled nucleotides which results in the maximum detectability of the oligonucleotide.

"Specific fluorescence" refers to the quantum efficiency per unit mass of labeled nucleic acid, or the amount of fluorescent label incorporated per unit mass of labeled nucleic acid.

"Specific detectability" refers to the amount of label incorporated per unit mass of labeled nucleic acid.

"Optimal fluorescence" refers to the maximum specific fluorescence which can be obtained in a given reaction medium, and it is based on the optimal spacing of the fluorescent moieties in the oligonucleotide and the polymerase chosen for a particular fluorescently labeled nucleotide.

"Optimal detectability" refers to the maximum specific detectability, e.g. fluorescence, which can be obtained in a given reaction medium, and it is based on the optimal spacing of the label molecules in the oligonucleotide and the polymerase chosen for a particular labeled nucleotide.

"Primer extension" refers to the template directed, polymerase driven process of extending a primer oligonucleotide which is base paired to a template with nucleotide triphosphates, such that the final product is a (fully or partially) duplex DNA strand.

A "target sequence" is that oligonucleotide sequence which is to be labeled (either covalently or non-covalently), coupled or ligated to an optimally fluorescent moiety.

The process of "nick-translation" is catalyzed by DNA polymerase, and it is characterized by the simultaneous polymerization of new DNA and the degradation of DNA ahead of the growing site.

A "DNA matrix (or matrices)" refers to successive layers of polynucleotides of specific structure, including a double-stranded waist and single stranded, free arms at the molecule ends, formed by hybridization of the arms to adjacent molecule arms. Such matrices are described in U.S. Pat. Nos. 5,175,270 and 5,487,973, which are incorporated herein by reference.

"Specific activity" refers to that amount of radiolabel present per unit mass of labeled compound, and it is usually expressed in units of Curies (Ci) per millimole (mmol).

The process known as a "Southern blot" enables the detection of specific sequences of a nucleic acid to be detected by a labeled probe. When the label is radioactive the result is visualized by autoradiography. The restricted DNA fragments are denatured in a gel and blotted onto a sheet of membrane nitrocellulose or nylon by capillary action or electrophoretic transfer in a manner that preserves the original pattern. After the single-stranded DNA is permanently bound to the membrane, the sheet is incubated in a solution containing labeled probe (i.e., complementary DNA or RNA). Once the homologous sequences have had time to anneal, the membrane is washed free of unhybridized probe. The resulting autoradiograph, for radioactive probes, will indicate which restriction fragments bear homology to the nucleotide sequence on the probe.

Similarly, a "Northern blot" is the analogous process whereby specific sequences of RNA are detected by a labeled probe. The RNA is blotted onto a membrane, and the sheet is incubated in a solution containing labeled probe. After the complementary sequences have annealed, the medium is washed free of unhybridized probe and the label is detected. The result will indicate which RNA fragments bear homology to the nucleotide sequence on the probe.

A nucleic acid "dot blot" is produced when a nucleic acid in solution is detected by spotting the solution on a membrane and detected as in a Southern or Northern blot. Dot blots can be used to quantitate the amount of nucleic acid in an extract.

"Random priming" refers to the process whereby double stranded DNA is denatured in the presence of random primers, and unlabeled nucleotide triphosphates, $^{32}$P-labeled nucleotide triphosphates and polymerase are added to initiate elongation of the primer, followed by denaturation to release labeled probe.

A "microtitre plate assay" refers to the detection of an antigen-antibody, dye-substrate or probe-target interaction between a solution of unknown concentration of antigen, protein or DNA/RNA. The unknown solution is placed in a microtitre plate, which consists of individual wells for small volumes (usually no more than 200 $\mu$l), and is reacted with an antibody solution, dye or probe of known concentration. The degree of interaction between the reactant and unknown solution is indicative of the concentration of the solute present in the unknown solution. The interaction can be assessed by fluorescence, ultra-violet absorption, or reaction with a secondary antibody solution.

A "label" or "labeling moiety" is any compound employed as a means for detecting an oligonucleotide. The label or labeling moiety is attached to an oligonucleotide via ionic or covalent interactions, including hydrogen bonding, electrostatic interactions and intercalation. Examples of labels and labeling moieties include, but are not limited to fluorescent dye conjugates, biotin, digoxigenin, radionucleotides, antibodies, enzymes and receptors, such that detection of the labeled oligonucleotide is by fluorescence, conjugation to streptaniden and/or avidin, antigen-antibody and/or antibody-secondary antibody interactions, quantitation of radioactivity, catalytic and/or ligand-receptor interactions.

The method of the present invention generates labeled oligonucleotides with a known number and spacing of labeling moieties in the sequence. The oligonucleotides of the present invention may be represented by the formula: $N^t (N^t)_n N^t$ where n is an integer from 20 to 1000; wherein all nucleotides in the sequence are capable of forming a base pair with an optimally labeled-conjugated nucleotide triphosphate. Hence, the corresponding optimally labeled oligonucleotide may be represented by the formula: $N^f (N^f)_n N^f$ where n is an integer from 20 to 1000; wherein $N^f$ represents an optimally labeled nucleotide in the sequence.

Additionally, oligonucleotides of the present invention may be represented by the formula: $N^t (N_m N^t)_n N_m$ where n is an integer from 20 to 1000, and m is an integer from 1 to 11; wherein nucleotide $N^t$ is capable of forming a base pair with an optimally labeled dye-conjugated nucleotide triphosphate, and nucleotide, N, is not capable of forming such base pairs.

Hence, the corresponding optimally labeled oligonucleotide may be represented by the formula: $N^f (N_m N^f)_n N_m$ where n is an integer from 20 to 1000, and m is an integer from 1 to 11; wherein nucleotide $N^f$ represents a labeled nucleotide in the sequence, and nucleotide N, is not labeled.

The labeling of the target sequence with the labeling moiety can be done prior to or during the incorporation of the target sequence to the oligonucleotide. When the labeled oligonucleotide is generated prior to the incorporation of the target sequence, the target sequence can be attached to the labeled oligonucleotide by primer extension or ligation. Alternatively, the labeling moieties can be incorporated with the target sequence during the polymerization reaction between the target and an appropriate template, with the addition of dye-conjugated nucleotide triphosphates (NTPs) in addition to unlabeled NTPs, by cloning or randomer extension.

The process begins with the determination of the optimal spacing and preferred polymerase for each dye-NTP conjugate. In general, a primer sequence (preferably 6–40 bases long) and multiple template sequences will be required. The template sequences (20–100 bases) will have a primer binding region and downstream from the primer binding region the appropriate nucleotide ("G" for "C" conjugated dyes, "A" for "U" conjugated dyes, etc.) spaced every base (polyhomonucleotide in a first template sequence), every other base in a second template sequence, every third base, every forth base, every fifth base, every sixth base, every seventh base, every eight base, every ninth base, every tenth base or every eleventh base. The repetition of nucleotide in this manner is referred to herein as a nucleotide repeat region, and it can be represented by the following formula: $N_{(0-11)}N^r$ where N represents a nucleotide which is not capable of forming a base pair to a label-conjugated nucleotide; $N^r$ represents the nucleotide which is capable of forming a base pair to a dye-conjugated nucleotide, or that which is directly conjugated to the label. The spacing of the label-conjugated nucleotides within the nucleotide repeat region should be as close as possible without quenching the detection of the individual moieties. The intervening sequence can be repeated sequence, semi-repeated, or random sequence selected from the three non-basepairing (to the dye-NTP) bases. The primary constraint on the intervening sequence is the absence of self homology, either intertemplate or intratemplate to minimize non-specific priming events. A single set of primers is sufficient for determining the optimal spacing for any dye-NTP conjugate.

The primer should be radiolabeled, preferably with $^{32}P$, to high specific activity, and the actual specific activity should be determined by counting an aliquot of the radiolabeled primer and measuring the optical density at 260 nm. The actual determination of the specific activity may be omitted if the optimal spacing is the only information desired from the experiment; however, determination of the specific activity allows for rapid subsequent determination of the specific detectability. The $5'$-$^{32}P$ labeled primer and templates (in a separate reaction for each template sequence) should be mixed in approximately stoichiometric ratios, and allowed to anneal. The annealing process can be done in any buffer conducive to the formation of nucleic acid hybrids, such as 100 mM Tris-HCl, pH 8.0, 200 mM NaCl, 1 mM EDTA. After annealing, the sample can be precipitated with ethanol and resuspended in water, or alternatively used directly in the polymerization assay.

An aliquot, approximately 1 $\mu$g, of annealed primer-template should then be added to a series of reactions using multiple polymerases, such as SEQUENASE™ from Amersham Life Sciences, Klenow fragment of DNA Pol I, Taq Polymerase, Pyrostase, and other commercially available polymerases. The reaction should take place in the optimized buffer for each particular polymerase (as determined by the manufacturer). The reaction should also contain the dye-NTP, and unlabeled NTPs at a concentration of 20 MM to 2 mM (excluding the NTP which is already added as a part of the dye-NTP conjugate). Each polymerase is capable of recognizing and incorporating the dye-NTP conjugates into the polymerization reaction to a different degree, and the choice of enzyme may significantly affect the specific detectabilty of the labeled probe.

Following the polymerase reaction, the labeled oligonucleotides should be purified away from the unincorporated nucleotide triphosphates. The purification can be accomplished by ethanol precipitation, size exclusion chromatography, gel electrophoresis or another method. The purified labeled oligonucleotides should be quantitated by scintillation counting or, if sufficiently large quantities are available, by measuring the optical density at 260 nm and by means suitable to any detect the label, e.g., measuring.

The specific detectability of the purified labeled oligonucleotides is then determined. A known aliquot of the labeled oligonucleotide is diluted in reagent grade water and the amount of label determined using any means necessary to quantitate the amount of label present. The reaction mixture showing the greatest specific detectabilty is selected as the optimal labeling method for that particular dye-NTP conjugate.

Alternatively, the methods of the present invention can be used for labeling ribonucleotide sequences, in which case, RNA polymerase and labeled ribonucleotides would be used in the synthesis of optimally labeled oligonucleotides.

Labeling of a Target Sequence

The optimal spacing and the polymerase needed for a particular dye-NTP conjugate are selected as described hereinabove. Subsequently, target sequences may be labeled by the optimally labeled oligonucleotide by ligation of the target sequence to labeled nucleotides, cloning the target sequence adjacent to the optimal spacing sequence or by "randomer" extension reaction.

Labeling a Target Sequence by Ligation

Labeling by ligation is accomplished by first synthesizing and purifying an optimally labeled nucleic acid (20 bases to 2 kilobases). The target sequence for labeling with the labeled oligonucleotide is nicked into small pieces, which average 30–70 bases, by chemical degradation or by treatment with nuclease such as DNAse I or a restriction enzyme. Approximately equal weights of labeled oligonucleotide (typically 50 ng to 5 $\mu$g in 50–100 $\mu$l total reaction volume) and target sequence are reacted in ligation buffer as recommended by the ligase enzyme manufacturer. The relative success of the ligation step can be assessed by gel electrophoresis. The ligated material can be directly used in hybridization assays or, if desired, purified by precipitation, size fractionation, gel electrophoresis, antigen-specific binding, or another method.

Labeling a Target Sequence by Randomer Extension

The basis of this labeling technique is the use of a short (6–12 base) random sequence at the 3' end of the optimally labeled oligonucleotide. The initial labeling reaction of the template with label is modified such that the template molecule is designed to have a 5' overhang (the extension region for incorporation of dye-NTP) as well as a 3' overhang of 6–200 bases with the most 3' sequence being a random sequence of typically 6–12 bases. The purified labeled oligonucleotide may be used directly in the primer extension reaction or preferably crosslinked with trimethylpsoralen prior to use in the target labeling reaction.

The target labeling reaction consists of denaturing the desired target sequence, adding the polymerase, an excess of labeled-primer molecules and the appropriate NTPs for the desired polymerase (i.e. dATP, TTP, dCTP, dGTP for use with Klenow polymerase), in the appropriate buffer. Some of the 3' ends of the labeled randomer will serve as primers on the target molecule thereby being extended during the polymerization process and generating molecules having a 3' end complementary to the target molecule and an optimally labeled 5' end.

Labeling of a Target Sequence Following Cloning

By cloning the optimized template sequence downstream from the SP6, T3, or T7 promoter sites, and then cloning a target sequence further downstream from the promoter sequence, subsequent polymerase labeling cogenerates polynucleotides having the optimally labeled sequence and the target sequence. The polymerase may be an RNA polymerase, such as T7 RNA polymerase for use with ribonucleotide triphosphates. The polymerase may also be a DNA polymerase and the labeling performed by specific primer extension or via random priming methods.

The labeled nucleic acids may be used as probes for a particular sequence wherever highly labeled nucleic acid probes are desired, e.g., in known nucleic acid assay methods such as dot blot, Southern blot or Northern blot, etc. In addition, the labeled oligonucleotides may be used for in situ hybridization techniques, wherein the sequence of interest is present in only a small number of cells within a large mixed population. Such sequences may be undetectable in tissue extracts due to the presence of interfering sequences from surrounding tissue.

In situ hybridization may be used to: (1) identify sites of gene expression; (2) analyze the tissue distribution of transcription (3) identify and localize viral infection; (4) follow changes in specific mRNA synthesis; and (5) aid in chromosome mapping. The present invention can provide increased specific detectability and therefore, enhanced sensitivity when compared to conventional methods for in situ hybridization.

Another use for the present invention is for the enhanced detection of nucleic acid sequences in combination with DNA matrices, which are disclosed in U.S. Pat. Nos. 5,175,270 and 5,487,973, the contents of which are incorporated herein by reference.

"Dymontor dendrimers" are dynamic molecules assembled from monomeric subunits of DNA, having arms organized at a surface layer with the capacity to bind target as well as multiple labels, which results in amplified signal. Unrestricted torsion of these surface arms, the result of a large volume to mass ratio, greatly facilitates interaction with target.

Dymontor dendrimers amplify signal in a variety of techniques, including blot assays and fluorescence detection. Independent of the signal molecule, the dendrimer will amplify signal because a single dendrimer carries multiple signal molecules. The ability of nucleic acids to recognize and specifically bind to complementary sequence is the basis of dymontor dendrimer technology.

Dymontor dendrimers are assembled via sequential hybridization of uniquely designed single DNA strands. Pairwise hybridization of the single strands result in the formation of "monomers" which have four single stranded "arms" and a double stranded "waist". The molecule grows exponentially with each sequential layer of hybridization. Dymontor dendrimers have been assembled ranging in size from a few hundred bases (a 1-layer dendrimer having twelve surface arms) to several million bases (a 12-layer dendrimer having 2,125,764 surface arms).

The outer surface of each dendrimer has 2 types of arms, one used to bind target and the other used to bind signal. Dymontor dendrimers with one to six layers can be described as existing in a sphere that is greater than 99% aqueous solvent. This large volume to mass ratio creates an extraordinary open structure, engendering readily accessible arms on the dendrimer to which target can bind.

DNA dymontor dendrimers amplify signal in nucleic acid blot formats. The gain in signal is achieved simply by the inclusion of a single additional component to the standard blot system, i.e., the DNA dymontor dendrimer. In all other respects, the protocol remains unchanged. Dendrimers are given specificity for a target, labeled and added to the hybridization mixture. Labeling can be done using standard techniques, e.g., radioactive isotopic labeling, e.g., using radioactive phosphorus, biotin, digoxigenin, fluorescent molecules, or enzymes, such as alkaline phosphatase and horseradish peroxidase.

Using dymontor dendrimers, one can routinely achieve 50 to 100-fold signal enhancement, when compared to identical blots probed with specific oligonucleotide alone.

Specificity to a particular sequence target is attached to a dendrimer in a manner similar to the assembly of dendrimer itself. For instance, to make a target specific dendrimer, two reagents are needed: the core 4-layer dendrimer and an oligonucleotide complementary to both the target and to the dendrimer sequence. A 4-layer dendrimer has 324 arms available for binding on its outer surface, one half of the arms with a(+)– sequence, and the other half of the arms with c(+) sequence (see FIG. 1A). Typically, only one type of the outer arms is used to confer specificity to a particular target. An oligonucleotide made of a(–) sequence and sequence complementary to the target is hybridized to 4-layer dendrimers via the a(+) sequence on the outer surface to yield 4-layer target specific dendrimers.

Figure 1B:
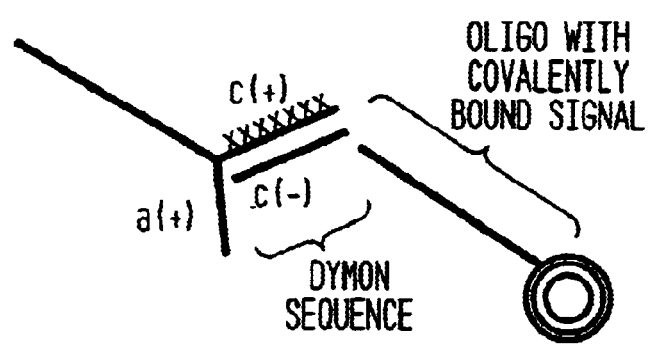

As shown in FIG. 1B, label can be attached to dendrimers in a manner similar to the attachment of target sequences. For a core 4-layer dendrimer with 324 arms available for binding on its outer surface (one half with a (+) sequence and the other half with c(+) sequence), the arms which are not to be hybridized to target will be hybridized to labeled oligonucleotide. An oligonucleotide, part of which is complementary to dendrimer sequence, i.e. c(–) sequence, and part of which is covalently bound to label, would by hybridized to 4-layer dendrimers via the c(+) sequence on the outer surface, yielding labeled 4-layer dendrimers. Many labels can be used, including but not limited to, radioactive isotopics, e.g., $^{32}P$, biotin and digoxigenin. Target specific dendrimers deliver hundreds of labels when hybridized to the target.

Figure 2:
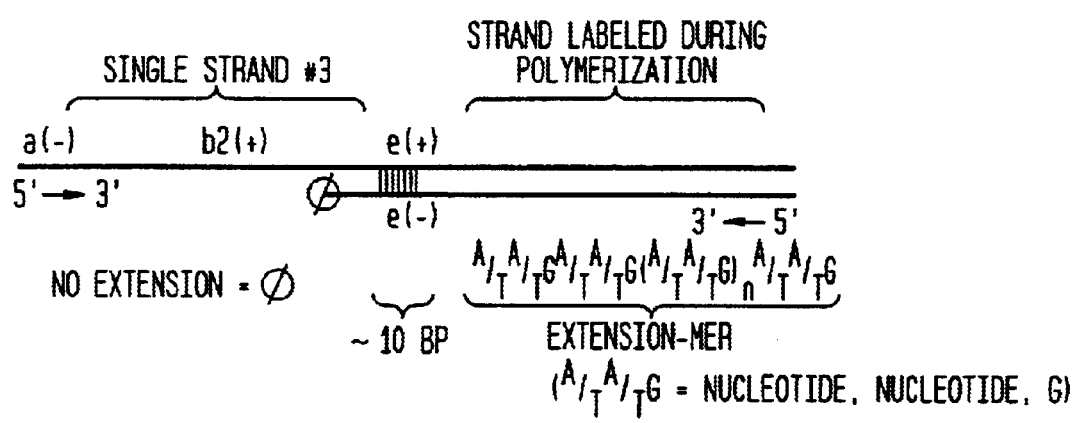
FIG. 2 is a schematic representation of dendrimer labeling via extension reaction.

FIG. 2 shows dendrimer labeling via extension reaction. Briefly, one of the single stranded DNA oligonucleotides used to make the core dendrimer is hybridized at its 3' end to an extension-mer designed with only three bases: A, T and G. The intension of the design is for the single stranded DNA to extend while the extension-mer does not.

To a reaction mixture containing single stranded oligonucleotide and extension-mer, is added: polymerase, dATP, dTTP and labeled dCTP. Since dGTP is absent from the mixture, the first time the base "C" is encountered, extension will abort. In this reaction, "C"s are found only in the single stranded DNA's used to make core dendrimer, and by design, not in the extension-mer. Therefore, extension will proceed from the 3' end of the dendrimer signal strands, but will be curtailed from the 3' end of the extension-mer. The extended, labeled strand is purified on a G50-Sephadex column, hybridized via the a(–) sequence by the method described above. Labeled dCTP is incorporated into the extension-mer each time the base "G" is encountered. dCTP can be labeled with $^{32}P$ ($\alpha^{32}P$-dCTP), fluorescent moieties, such as Texas Red™, rhodamine, fluorescein, Cy$_3$™, Cy$_5$™, and other art-recognized, suitable labels.

Core dymontor dendrimers can be fluorescently labeled via the extension reaction, and these fluorescently labeled dendrimers can be subsequently visualized as individual molecules by fluorescence microscopy.

The method of the present invention, i.e., optimal labeling of oligonucleotides may be used in connection with dymontor dendrimers to produce an enhanced means of detecting a sequence of interest. In one embodiment, the optimally-labeled oligonucleotide probes of the present invention can be hybridized to the non-annealed, free, single-stranded arms of the DNA dendrimers, and the resultant optimally labeled dendrimers can be useful in the assay of a wide variety of nucleic acid sequences including those associated with pathogenic bacteria and viruses.

Finally, the present invention can be used in a microtitre plate assay system based on the quantitation of label, e.g. fluorescence, wherein the high specific fluorescence provided by the optimally fluorescent oligonucleotide probes would enhance and facilitate the detection of the fluorescent moiety in the assay.

The following non-limiting Examples are given by way of illustration only and are not to be considered a limitation of this invention, as many apparent variations of which are possible without departing from the spirit or scope thereof.

EXAMPLE 1

Fluorescence Optimization of the Incorporation of dCTP-Cy$_3$

In this example the polymerase and optimal spacing was determined for dCTP-Cy$_3$ incorporation. In addition, it was desirable that the fluorescently labeled strand be longer than the template strand so the primer sequence had a 5' overhang relative to the template strand. The template therefore utilized only three bases, "G", "A", and "T", so that "back" reaction (extension of the template sequence on the primer sequence) could be blocked by omitting dGTP from the reaction buffer. By designing the reaction to allow a 5' overhang on the primer strand, subsequent strand separation could be readily achieved by denaturing gel electrophoresis, since in the post reaction, the extension product is longer than the template sequence.

The templates were 4lmers designated a(+)−2C, a(+)−3C and a(+)−4C, each designed to incorporate the dCTP-Cy$_3$ dye every other, every third, or every fourth base respectively. The primer sequence was a 3lmer designed to hybridize with the template strand over 14 bases. Full extension of the primer was expected to yield a S8mer, with 27 bases added by the polymerase reaction.

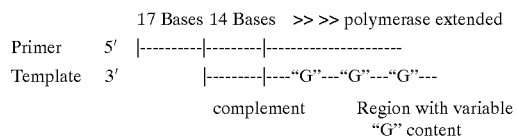

The synthetic oligonucleotides were purchased from The Midland Certified Reagent Co., Midland, Tex. and were dissolved in reagent grade water at a concentration of 200 ng/µl (based on 30 µg/ml=1 A260U). The primer sequence was 5' labeled with $^{32}$P by γ$^{32}$P-ATP (ICN Radiochemicals Cat #35020) 100 uCi/reaction and 1OU of polynucleotide kinase (Boehringer Mannheim Biochemicals) in the manufacturer's supplied reaction buffer and recommended reaction time. The primer was purified essentially free of unincorporated nucleotide by size exclusion chromatography (select-D-G25 Column 5'-3'®, Boulder, Colo.) as recommended by the manufacturer, and it had a specific activity of 31,180 cpm/ng. The primer was stored in aliquots, each at a concentration of 62.2 ng/µl (as determined by the OD$_{260}$ of 58.3 µl in 1 ml of reagent grade water) in 100 mM Tris-HCl, pH 8.0, containing 200 mM NaCl and 1 mM EDTA.

The annealing reaction was carried out by reacting 254 template oligonucleotide (5 µg, 0 cpm) and 49 µl $^{32}$P labeled primer (3.0 µg, 39,540,000 cpm) in 24 µl reagent grade water containing 2.0 µl 5 M NaCl (final concentration of 100 mM NaCl). The reaction was cooled from 95° C. to room temperature over 15 minutes in a 1 L beaker.

The subsequent polymerase extension reaction was carried out by combining 10.0 µl of the aforementioned annealed oligonucleotide reaction mixture, 10 µl 5×reaction buffer (supplied by the manufacturer of the polymerase), 1 µl dATP, 1 µl dTTP (each 10 mM, supplied by Boehringer Mannheim), 5.0 µl dCTP-Cy3 (1 mM, supplied by Biological Detection Systems), 22 µl reagent grade water and 1 µl SEQUENASE™ (USB United States Biologicals, 10 units) or Klenow fragment of DNA Poll (supplied by Boehringer Mannheim, 10 units). The reaction was complete after 1 hour at room temperature.

A portion of each reaction was loaded on a 9% denaturing polyacrylamide gel. Following electrophoresis, the gel was dried on 3 MM paper and exposed to x-ray film for autoradiography. Then, a separate aliquot from each of the reactions was loaded on a preparative 9% denaturing acrylamide gel, electrophoresed, and stained with ethidium bromide. The labeled (5' $^{32}$P and 3' Cy$_3$-CTP at varying spacing) 58mers were excised from the gel, triturated with 200 µl 10 mM Tris-HCl, pH 8.0, containing 1 mM EDTA, and the samples were shaken overnight in 1.5 ml microcentrifuge tubes at 37° C. The samples were briefly centrifuged and the supernatant was transferred to a fresh microcentrifuge tube. An aliquot of each supernatant was counted in a Beckman L58100 scintillation counter. Equal counts (10,000 cpm-854 pg of DNA as 30mer a(−)) were added to 2 ml of reagent grade water and scanned for fluorescence with a SPEX instruments Fluoromax spectrofluorometer.

Excitation was found to have maximum signal to noise ratio at 535 nm. Emission was determined over the range of 560 nm to 620 nm. Emission maxima were centered around 565 nm and the emission maximum for each reaction was determined for the calculation of the specific fluorescence. The results are shown in Table 1.

TABLE 1

Specific Fluorescence as a Function of Polymerase

| Sample | Maximum Fluorescense cps | Specific Fluorescence cps/pg |
| --- | --- | --- |
| Klenow Rxn 2C | 125,000 | 146 |
| Klenow Rxn 3C | 99,000 | 116 |
| Klenow Rxn 4C | 160,000 | 187 |
| Sequenase Rxn 2C | NR* | NR* |
| Sequenase Rxn 3C | 1,367,000 | 1,600 |
| Sequenase Rxn 4C | 1,020,000 | 1,200 | where cps = counts per second; and pg = picogram
*no polymerization could be detected, i.e., no measure of specific fluorescence The above analysis demonstrates that the choice of enzyme can have a significant effect on the resulting specific fluorescence, and the spacing of the dye incorporation is important for maximizing the specific fluorescence. For the dye-nucleotide conjugate, dCTP-Cy$_3$, the optimal enzyme is SEQUENASE™ and the optimal spacing is every third molecule.

EXAMPLE 2

Incorporation of Optimally Fluorescent Oligonucleotide with DNA Matrix

The 3C optimally fluorescent oligonucleotide can be used to label the outer layer of polynucleotides of a DNA matrix, through their non-annealed, free, single-stranded arms. The fluorescently labeled DNA matrix can be used to recognize the multiple DNA arms of the sequence bound to a smaller bead, and to supply an easily measured mass to the assay system.

First, the DNA bead matrix is assembled as described in U.S. Pat. No. 5,487,973. Sequential additions of matrix monomers leads to a DNA matrix with k layers (k-Mmer). The double-stranded, unpurified 3C optimally fluorescent oligonucleotide (which has a 5' single-stranded overhang) is added as the final addition to the k-Mmer, yielding a DNA bead matrix having optimally fluorescent single-stranded arms. The annealing reaction is performed in 2×SSPE (20× SSPE=3.6 M NaCl, 0.2 M sodium phosphate, pH 7.0, and 0.02M EDTA).

EXAMPLE 3

DOT Blots with Target Specific Dendrimers

Figure 3A:
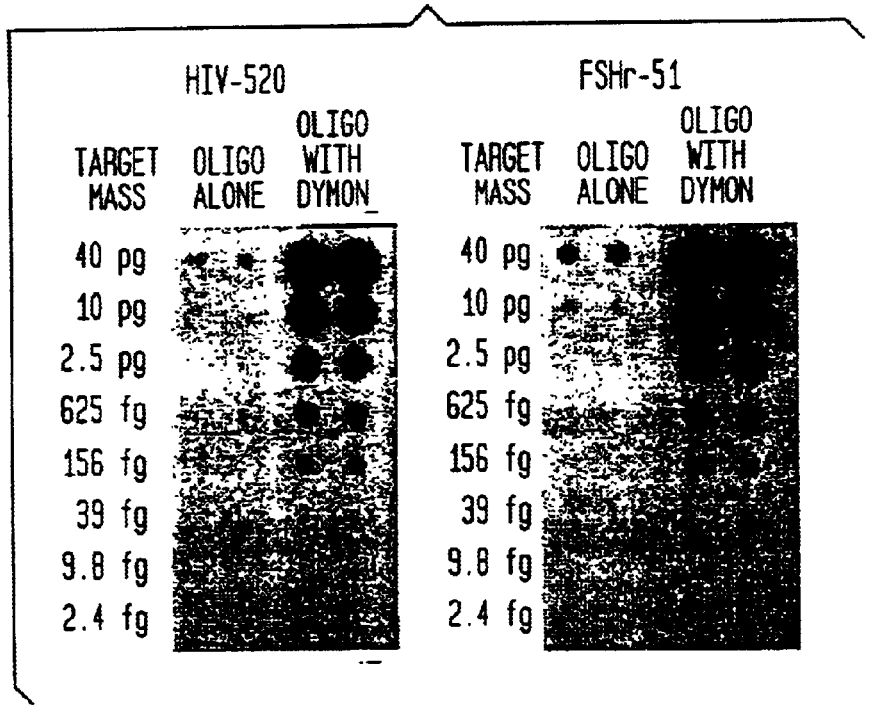
FIG. 3A is a dot blot with target specific dendrimers optimally labeled with $^{32}$P, wherein the target sequence is HIV520 and FSHr-51 (fragments of the human immunodeficiency virus and follicle stimulating hormone receptor, respectively)
Figure 3B:
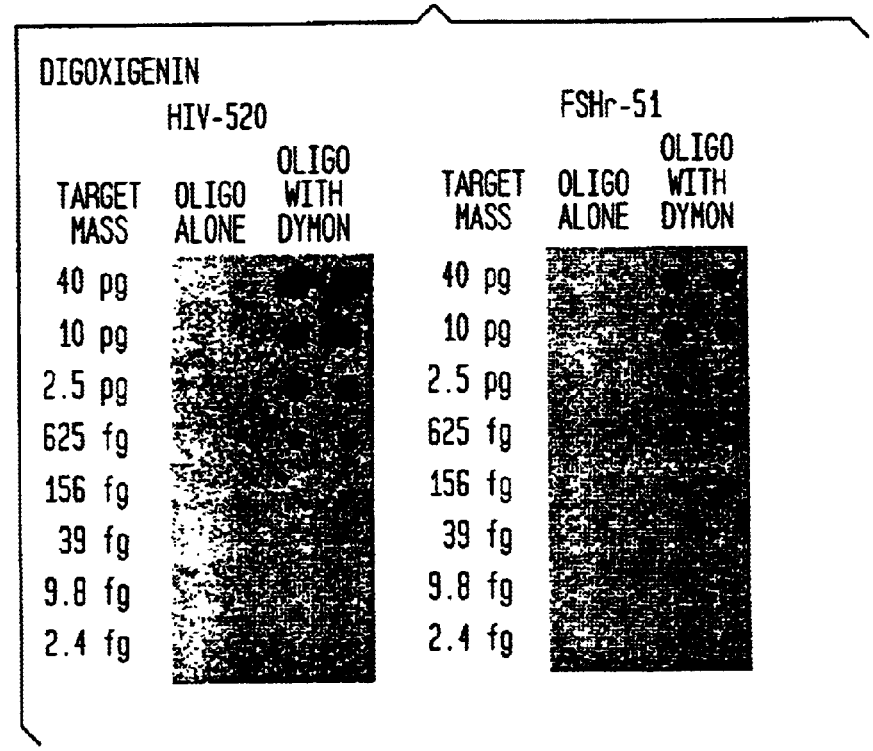
FIG. 3B is a dot blot with target specific dendrimers optimally labeled with digoxigenin, wherein the target sequence is HIV-520 and FSHr-51.
Figure 3C:
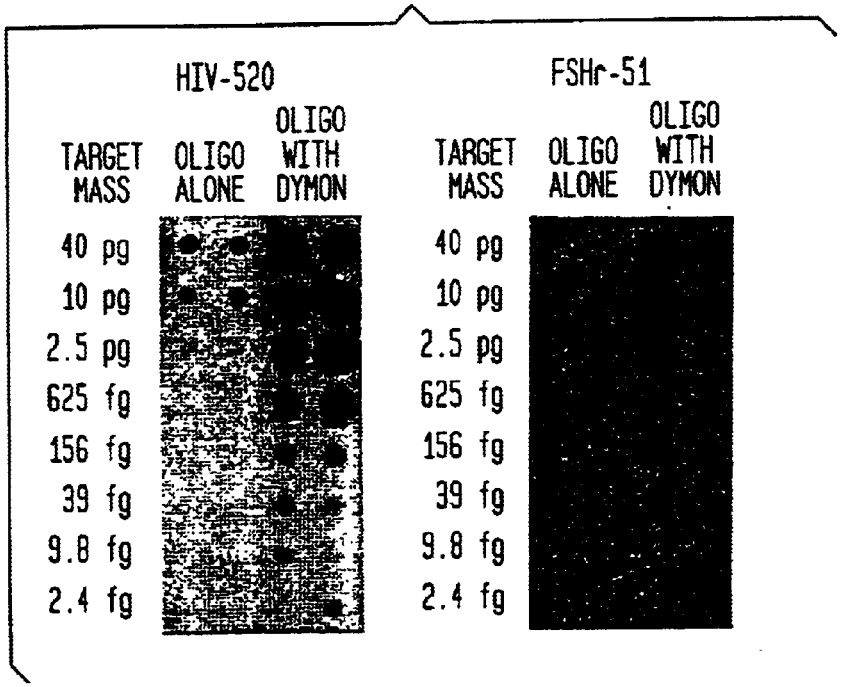
FIG. 3C is a dot blot with target specific dendrimers optimally labeled with biotin, wherein the target sequence is HIV-520 and FSHr-51.
Figure 3D:
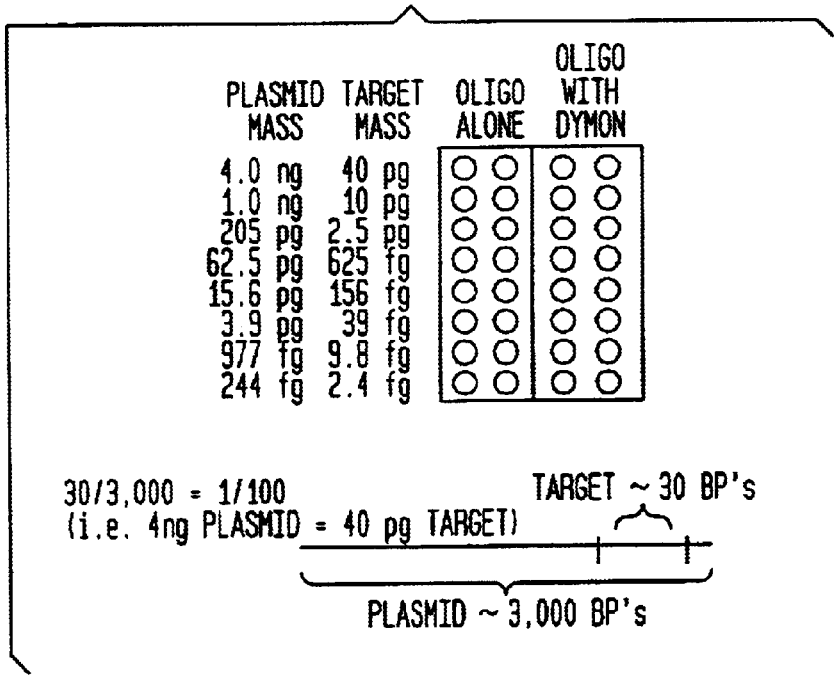
FIG. 3D is a schematic representation of the distribution of plasmid, target and oligonucleotide on the dot blot, and the design of the target specific probe.

Target plasmids were digested to yield single cut, linear molecules. Samples (in duplicate) were blotted directly to positively charged membrane. optimally labeled oligonucleotide and target specific DNA dendrimers were prehybridized for 30 minutes at 80° C., followed by hybridization to membranes for approximately 15 hours at 65° C., and then 1.5 hours at 45° C. All washes were done at 50° C., 3×10 minutes in 2×SSC 0.1% SDS, followed by 2×20 minutes in 0.5×SSC 0.1% SDS. Target specific dendrimers were hybridized to the target sequences in approximately stoichiometric masses. The optimally labeled oligonucleotides were labeled according to the method of the present invention using $^{32}$P (FIG. 3a), digoxigenin (FIG. 3b) and biotin (FIG. 3c), and the target specific, optimally labeled dendrimers were used to detect HIV-520 and FSHr-5 (while the dendrimers are designated by the first base of the probe, i.e., HIV 520 detects the HIV LTR from position 520–620, the target of the optimally labeled dendrimer is whole HIV; similarly, the FSHr specific dendrimers detects a specific position of FSHr, but it is used as a probe for whole FSHr). For each blot, lanes were prepared with identical amounts of specific target, left lanes were probed with specific labeled oligonucleotide alone, and right lanes were probed with target specific 4-layer DNA dendrimers and labeled oligos (as outlined in FIG. 3d). In all cases, optimally labeled oligo with dendrimer detected a smaller amount of target than the oligo alone, such that a signal increase of 50–100 fold was observed.

EXAMPLE 4

Southern Blots with Optimally-Labeled, Target Specific Dendrimers

Figure 4A:
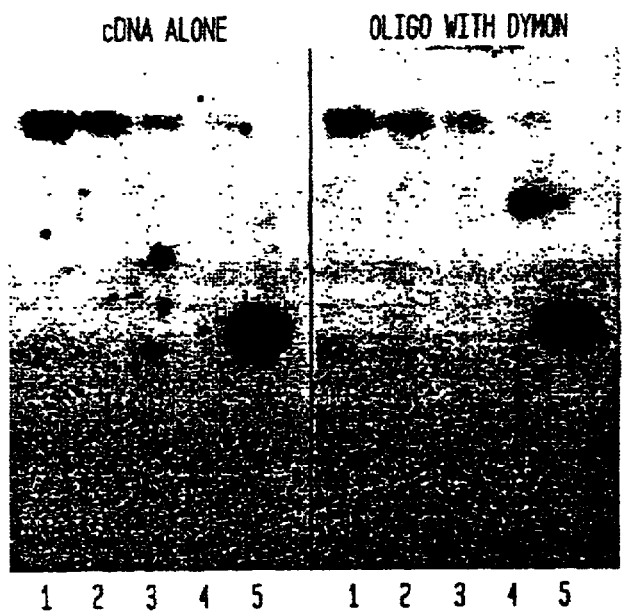
FIG. 4A is a Southern blot with target specific dendrimers using optimally $^{32}$P labeled cDNA or oligo with dendrimer.
Figure 4B:
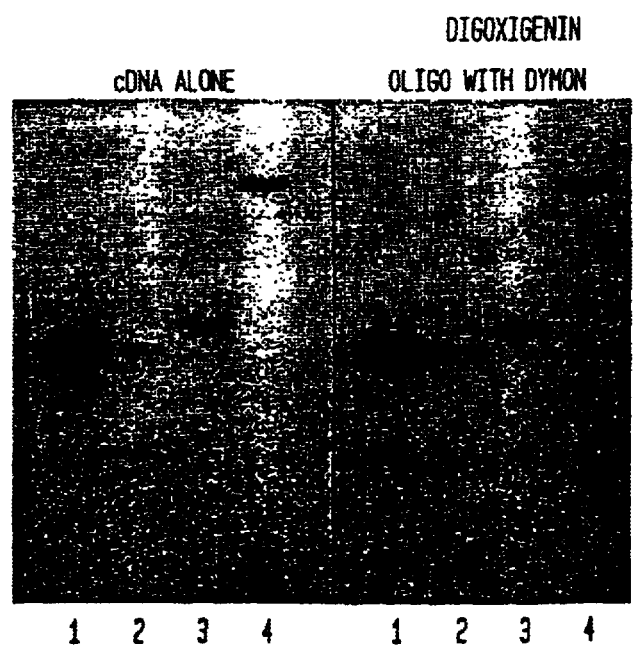
FIG. 4B is a Southern blot with target specific dendrimers using optimally digoxigenin labeled cDNA or oligo with dendrimer.
Figure 4C:
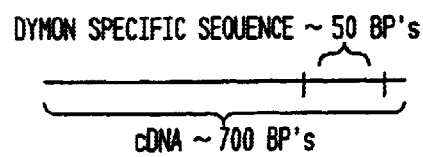
FIG. 4C is a schematic representation of the design of cDNA probes.

Duplicate samples of human genomic DNA and plasmid controls were digested with restriction enzyme, electrophoresed in agarose gels and stained with ethidium bromide. The DNA in the gels was acid nicked, denatured and neutralized prior to transfer to positively charged membrane. The membranes were prehybridized for 30 minutes at 80° C. Membranes were subsequently hybridized with probe for greater than 12 hours at 60° C. Probes were either target specific DNA dendrimers with optimally labeled oligonucleotide or optimally labeled via a random prime reaction in accordance with the present invention with $\alpha^{32}$P-dCTP or digoxigenin(dig)-dUTP. Specificity was added to the DNA dendrimers as described above. The FSHr cDNA probe was approximately 700 base pairs in length, while the FSHr sequence used to confer specificity on the DNA dendrimer was only 50 base pairs in length. The DNA dendrimer probe identified the identical bands detected by the FSHr cDNA probe using a target specific sequence only a fraction of the size of the cDNA probe. The results are shown in FIGS. 4a–c. In FIG. 4a, lanes 1 to 4 contain human genomic DNA digested with ECOR1; 8 µg, 2 µg, 500 ng and 125 ng, respectively, and lane 5 contains 50 pg of plasmid with FSHr sequence, labeled with $^{32}$P. In FIG. 4b, lanes 1 and 2 contain plasmid with FSHr sequence, 250 and 5 picograms, respectively, and lanes 3 and 4 contain 8 µg of human genomic DNA digested with Eco R1 and Pst I, respectively. For each blot, the left panel was probed with labeled cDNA alone, and the right panel was probed with target specific DNA dendrimers and optimally labeled oligonucleotides.

Having thus described in detail certain preferred embodiments of the present invention, it is to be understood that the invention defined by the appended claims is not to be limited by particular details set forth in the above description, as many apparent variations thereof are possible without departing from the spirit or scope thereof.

What is claimed is:

1. An oligonucleotide comprising a nucleotide sequence complementary to a primer, and a nucleotide repeat region downstream form said complementary sequence, wherein said nucleotide repeat region comprises at least one detectably labeled nucleotide, each of said at least one detectably labeled nucleotide containing the same detectable label, and wherein said nucleotide repeat region also comprises a plurality of nucleotides that are not detectably labeled.

2. The oligonucleotide of claim 1, wherein said detectable label comprises a fluorescent dye.

3. The oligonucleotide of claim 1, wherein said detectable label comprises a radiolabel.

4. The oligonucleotide of claim 3, wherein said radiolabel is $^{32}$P.

5. The oligonucleotide of claim 1, which is single-stranded.

6. The oligonucleotide of claim 1, which is double-stranded.

7. The oligonucleotide of claim 1, which contains from about 20 to about 1000 total nucleotides.

8. An optionally labeled oligonucleotide, comprising a detectably labeled nucleic acid sequence and a nucleotide repeat region, wherein the nucleotide repeat region comprises at least one nucleotide that is conjugated to a detectable label, and a plurality of nucleotides that are not conjugated to a detectable label, wherein each of said at least one detectably labeled nucleotide contains the same detectable label.

9. The oligonucleotide of claim 8, wherein said detectable label comprises a radiolabel.

10. The oligonucleotide of claim 9, wherein said radiolabel is $^{32}$P.

11. The oligonucleotide of claim 8, which is single-stranded.

12. The oligonucleotide of claim 8, which is double-stranded.

13. The oligonucleotide of claim 8, which contains from about 20 to about 1000 total nucleotides.

14. The oligonucleotide of claim 8, wherein the detectable label comprises a fluorescent dye.

15. The oligonucleotide of claim 8, wherein the detectable label comprises biotin.

16. The oligonucleotide of claim 8, wherein the detectable label comprises digoxigenin.

17. The oligonucleotide of claim 8, wherein the detectable label comprises an antibody.

18. The oligonucleotide of claim 8, wherein the detectable label comprises an enzyme.

19. The oligonucleotide of claim 8, wherein the detectable label comprises a receptor.

20. The oligonucleotide of claim 8, wherein the detectable label comprises streptavidin.

21. The oligonucleotide of claim 8, wherein the detectable label comprises avidin.

\* \* \* \* \*